United States Patent [19]

Sander

[11] Patent Number: 4,946,784

[45] Date of Patent: Aug. 7, 1990

[54] SPHERICAL BIOCATALYST CONTAINING TITANIUM DIOXIDE PARTICLES

[75] Inventor: Ulrich Sander, Friedrichsdorf, Fed. Rep. of Germany

[73] Assignee: Metallgesellschaft Aktiengesellschaft, Frankfurt am Main, Fed. Rep. of Germany

[21] Appl. No.: 154,175

[22] Filed: Feb. 9, 1988

[30] Foreign Application Priority Data

Feb. 13, 1987 [DE] Fed. Rep. of Germany ....... 3704478

[51] Int. Cl.$^5$ .................... C12N 11/10; C12N 11/14; C12N 11/04; C12N 11/02
[52] U.S. Cl. .................................... 435/178; 435/176; 435/177; 435/182; 435/240.22
[58] Field of Search ............... 435/174, 176, 177, 178, 435/182, 240.22

[56] References Cited

U.S. PATENT DOCUMENTS

| | | | |
|---|---|---|---|
| 3,242,055 | 3/1966 | De Lucia | 435/176 |
| 4,218,363 | 8/1980 | Rohrbach et al. | 435/180 X |
| 4,266,029 | 5/1981 | Branner-Jorgensen | 435/176 |
| 4,291,909 | 7/1983 | Lin | 435/182 |
| 4,434,229 | 2/1984 | Nankai et al. | 435/176 X |
| 4,572,897 | 2/1986 | Amotz et al. | 435/178 X |
| 4,659,664 | 4/1987 | Buda | 435/178 X |

FOREIGN PATENT DOCUMENTS 0482149 1/1976 Australia.
1586364 3/1981 United Kingdom.

OTHER PUBLICATIONS

Enzyme Technology, pp. 219–235, Berlin, Heidelberg, New York, Tokyo, 1983.

*Primary Examiner*—David M. Naff
*Attorney, Agent, or Firm*—Sprung Horn Kramer & Woods

[57] ABSTRACT

Spherical biocatalyst particles having increased abrasion resistance are obtained containing a biologically active material such as a microorganism, $TiO_2$ particles having a size of 0.1 to 1 micrometer and an ionotropic biopolymer such as alginate, pectin, carrageenan or chitosan. The biocatalyst is prepared by forming a homogeneous degassed aqueous dispersion containing the biopolymer, 0.1 to 20% by weight of the biologically active material and 7 to 35% by weight of the $TiO_2$ particles, and dropping droplets of the dispersion from a nozzle into a precipitation bath containing polyvalent cations to precipitate the biopolymer and form spherical biocatalyst particles of 0.05 to 5 mm in diameter. The droplets may pass through a gas space containing an inert gas, air or reactive vapors such as acetaldehyde before reaching the precipitation bath. The $TiO_2$ particles may be surface-impregnated with $Al_2O_3$ and/or aluminum oxide hydrate.

7 Claims, No Drawings

SPHERICAL BIOCATALYST CONTAINING TITANIUM DIOXIDE PARTICLES

DESCRIPTION

This invention relates to a spherical biocatalyst, which consists of an immobilized, biologically active material and of an ionotropic, gellike matrix and to a process of producing the same.

Biocatalysts of the kind described first hereinbefore are known from the publication by Vorlop and Klein in Enzyme Technology, Third Rotenburg Fermentation Symposium 1982, Sept. 22 to 24, 1982, Springer-Verlag, 1983, pages 219 to 235. For instance, it has been stated in the publication that biocatalysts can be produced which are 0.1 to 4 millimeters in diameter and have good mechanical properties and consist of a crosslinked alginate matrix and of microorganisms (yeasts, bacteria). To produce the known biocatalysts, the alginates are dissolved in water and the aqueous solution is subsequently treated at an elevated temperature in an autoclave. Microorganisms are dispersed in the alginate solution and the resulting dispersion is dripped into a calcium chloride solution, in which the droplets remain for 30 to 60 minutes so that they are cured. Finally, the biocatalyst is separated and washed. It is also known from the publication that the biopolymers pectin, carrageenan and chitosan may be used as a matrix. Cells and enzymes rather than microorganisms can be immobilized as biologically active material in the matrix.

The known biocatalysts have been found to rise in the fermentation reactor and to form a coherent layer in the upper portion of the reactor because the catalyst beads have approximately the same density as the solution which is contained in the fermentation reactor and the solutes of which are to be reacted under the influence of the catalyst. The rise of the known biocatalysts will be particularly disadvantageous if the catalysts are used in a fermentation reactor which is operated to maintain a moving bed or fluidized bed. For this reason it is an object of the invention to provide a biocatalyst which has a higher density than water and which ensures an undisturbed operation of a fermentation process proceeding in a fluidized bed. The biocatalyst should also have a high resistance to abrasion and it should be possible to produce the biocatalyst under sterile conditions. Another object of the invention is to propose a process of producing the biocatalyst.

The object underlying the invention is surprisingly accomplished in that the matrix contains $TiO_2$ having a particle diameter from 0.1 to 1 micrometer. It has been found that the catalyst resists abrasion even in continuous operation and in a moist state has a specific gravity from 1.1 to 1.4 grams per milliliter. The $TiO_2$ has a large surface area having a $TiO_2$ content from 5 to 30% by weight and a high content of ion-active valences.

The biocatalyst in accordance with the invention will have particularly desirable properties if the $TiO_2$ particles are surface-doped with $Al_2O_3$ and/or $AlO(OH)$. To dope the $TiO_2$ particles they are sprayed with a 0.1- to 2-molar solution of an aluminum salt and are subsequently treated at 150° to 500° C. 10 to 50 grams of the aluminum salts, calculated as $Al_2O_3$, are used per kg of $TiO_2$. The heat treatment results in a hydrolysis of the aluminum salt so that $Al_2O_3$ and/or $AlO(OH)$ is formed, which is firmly anchored on the surface of the $TiO_2$ particles. Particularly $AlCl_3$ is used as an aluminum salt. It has been found that particularly the $TiO_2$ particles which are doped with $Al_2O_3$ and/or $AlO(OH)$ have on their surface free valences, which bond to the macromolecules of the matrix to form a highly stable solution.

A further feature of the invention resides in that enzymes, microorganisms or cells are used as a biologically active material and that the matrix consists of biopolymers, such as alginates, pectins, carrageenan or chitosan. It has been found that the biocatalyst in accordance with the invention will have good mechanical properties, a sufficiently high density and a high activity if the above-mentioned substances are used. Within the scope of the invention the biocatalyst has a particle diameter from 0.05 to 5 mm. Catalyst particles which are 0.5 to 5 mm in diameter are desirably employed for fermentation reactions which involve a formation or supply of gas. Catalyst particles which are 0.05 to 0.5 mm in diameter are preferred for fermentation reactions which do not involve a formation or supply of gas.

The object underlying the invention is also accomplished by the provision of a process of producing the biocatalyst, in which an aqueous solution of the substance for forming the matrix is mixed with 7 to 35% by weight $TiO_2$, 0.1 to 20% by weight biologically active material are admixed to the resulting mixture, the resulting dispersion is degassed under a pressure from 800 to 10 millibars and the degased dispersion is dripped from a nozzle into a precipitating bath. Particularly as a result of the degassing of the dispersion in the process in accordance with the invention, the biocatalyst has the desired specific gravity. All process steps are carried out at a temperature from 15° to 40° C. and sterile conditions can be maintained. The precipitating bath for biocatalysts having a matrix consisting of biopolymers, such as alginate, pectin or carrageenan consist of aqueous solutions of divalent or trivalent cations, particularly $Ca^{2+}$ or $Al^{3+}$. Chitosan-containing catalysts are precipitated by means of an aqueous solution which contains multivalent anions, particularly polyphosphates. Within the scope of the invention the solution of the substance for forming the matrix contains 70 to 99% by weight water. This will ensure a uniform admixing of the $TiO_2$ particles.

Within the scope of the invention it will be particularly desirable to cause the droplets emerging from the nozzle to fall freely through a gas space having a length from 0.2 to 2 meters and containing an inert gas or air, whereafter the droplets enter the precipitating bath. That measure will have the result that the droplets emerging from the nozzle have an almost spherical shape, which will not substantially change as they impinge on the precipitating bath. Within the scope of the invention it will also be particularly desirable to introduce reactive vapors, such as acetaldehyde, into the gas space so that said vapors will effect a surface-hardening of the catalyst beads. Temperatures up to 121° C. may be provided in the gas space because the residence time of the catalyst beads in the gas space is short and they are not inactivated by relatively high temperatures. Finally, within the scope of the invention the droplets which have emerged from the nozzle may remain in the precipitating bath for 0.1 to 24 hours. A cross-linking between the substance for forming the matrix and the multivalent ions contained in the precipitating bath is effected during that time. That cross-linking imparts to the droplets a strong structure. The hard catalyst spheres can be stored for several months and can desirably be used in a fluidized bed reactor. The catalyst spheres may optionally be activated with oxygen before they are used.

The subject matter of the invention will subsequently be explained more in detail with reference to an illustrative embodiment.

1635 kg twice-distilled water are mixed with 3.5 grams penicillin K so that an infection of the catalyst with extraneous germs will be inhibited for a long time. 300 kg of the yeast Saccharomyces cerevisiae having a solids content of 30% by weight are subsequently dispersed in the resulting mixture. 600 kg $TiO_2$ which has been treated with an aluminum salt and contains 2% by weight $Al_2O_3$, are then dispersed in the resulting mixture. A solution consisting of 1000 kg twice-distilled water, 60 kg sodium alginate, 360 g oleic acid, 180 g ergosterol and 2 liters of an emulsifying agent based on fatty acid are dispersed in the resulting suspension. Throughout the life of the catalyst, particularly while it is at rest, the oleic acid and the ergosterol act as a growth substrate.

The catalyst mixture is subsequently degassed in a vacuum vessel at 800 to 10 millibars and is slowly stirred as it is degassed. The degassed catalyst mixture is conveyed by means of compressed air or inert gas under a pressure of about 3 bars into a nozzle carrier, which is provided with a large number of capillary nozzles, each of which has an inside diameter of 0.8 mm. Air or inert gas flows around the capillary nozzles in an axial direction, from top to bottom, in the direction in which the droplets emerge, so that droplets having a defined size will be torn from the nozzles. The droplets fall through a gas space, which contains air and has a length Of 500 mm, and then impinge on the precipitating bath, which consists of twice-distilled water and 2% by weight $CaCl_2$. The precipitating bath has a height of 1000 mm and a spherical shape is assumed by the catalyst beads as they pass through the gas space and through the precipitating bath. The catalyst beads are withdrawn from the bottom of the precipitating bath and placed into a container, in which they are agitated for 12 hours in a solution consisting of twice-distilled water and 2% by weight $CaCl_2$. The catalyst beads are subsequently filled into barrels and are stored therein at 4° C. in a solution of 1% by weight $CaCl_2$. They can be stored for several months without an activity loss of the biocatalyst. 5000 liters of moist catalyst beads which are 2.5 mm in diameter and have a bulk density of 0.7 kg/l are obtained from the catalyst mixture.

The biocatalyst is used for the fermantation of glucose-containing substrates in the production of ethanol. Before the fermentation begins, the biocatalyst is activated with a 5% by weight glucose with an addition of air for 5 days. As a result, the yeast cells grow under the surface of the sphere in a dense growth zone of about 100 micrometers. The biocatalyst has a life of about 8 months in continuous operation.

I claim:

1. A spherical biocatalyst which consists essentially of at least one immobilized micro-organism, titanium dioxide particles having a diameter from 0.1 to 1 micrometer, and of an ionotropic biopolymer selected from the group consisting of an alginate, pectin, carrageenan and chitosan, said biocatalyst being produced by forming an essentially homogeneous degassed aqueous dispersion containing the biopolymer, 0.1 to 20 percent by weight of the micro-organism and 7 to 35 percent by weight of the titanium dioxide particles, dropping droplets of said disperson from a nozzle into a precipitation bath containing polyvalent cations to precipitate the biopolymer as spherical biocatalyst particles having a diameter of about 0.05 to 5 mm, and removing said spherical biocatalyst particles from said bath.

2. A biocatalyst according to claim 1, wherein the aqueous dispersion contains 70 to 99% by weight water.

3. A biocatalyst according to claim 1, wherein the droplets from the nozzle fall freely through an inert gas space having a length from 0.2 to 2 meters prior to contacting the precipitating bath.

4. A biocatalyst according to claim 3, wherein the gas space contains reactive vapors.

5. A biocatalyst according to claim 4, wherein the reactive vapors comprise acetaldehyde.

6. A biocatalyst according to claim 2, wherein the droplets are removed from the precipitating bath after 0.5 to 24 hours.

7. A biocatalyst according to claim 1, wherein the $TiO_2$ particles are surface-impregnated with $Al_2O_3$ and/or aluminum oxide hydrate.

* * * * *